US007002017B2

(12) United States Patent (10) Patent No.: US 7,002,017 B2
Klingler et al. (45) Date of Patent: Feb. 21, 2006

(54) ENANTIOSELECTIVE HYDROGENATION OF INTERMEDIATES IN THE SYNTHESIS OF TIPRANAVIR

(75) Inventors: Franz Dietrich Klingler, Griesheim (DE); Michael Steigerwald, Frankfurt (DE); Richard Ehlenz, Bad Kreuznach (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 10/797,313

(22) Filed: Mar. 10, 2004

(65) Prior Publication Data

US 2004/0224990 A1 Nov. 11, 2004

(30) Foreign Application Priority Data

Mar. 24, 2003 (DE) ................................. 103 13 118

(51) Int. Cl.
*C07D 405/12* (2006.01)
*C07D 309/32* (2006.01)

(52) U.S. Cl. .................................... 546/281.7; 549/292
(58) Field of Classification Search ................ 549/292; 546/281.7
See application file for complete search history.

(56) References Cited

FOREIGN PATENT DOCUMENTS

WO WO 99/12919 3/1999
WO WO 00/55150 9/2000

OTHER PUBLICATIONS

Jens Holz et al; Synthesis of a New Chiral Bisphospholane Ligand for the Rh(I)-Catalyzed Enantioselective Hydrogenation of Isomeric beta-Acylamido Acrylates; J. Org. Chem 2003 vol. 68 pp. 1701-1707; American Chemical Society.

Steve R. Turner et al; Tipranavir (PNU-140690): A Potent, Orally Bioavailable Nonpeptidic HIV Protease Inhibitor of the 5,6-Dihydro-4-hydroxy-2-pyrone Sulfonamide Class; J. Med. Chem 1998 vol. 41 pp. 3467-3476; American Chemical Society.

Copy of International Search Report Reference No. PCT/EP2004/002894.

*Primary Examiner*—Bernard Dentz
(74) *Attorney, Agent, or Firm*—Michael P. Morris; Mary-Ellen M. Devlin; Alan R. Stempel

(57) ABSTRACT

The invention relates to a process for preparing the compounds of general formula I

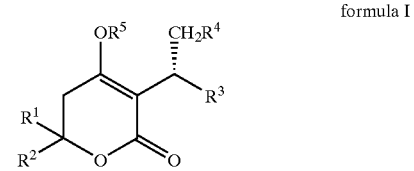

formula I by enantioselective hydrogenation of the compounds of formula II

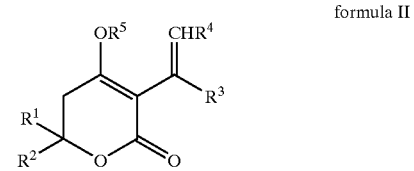

formula II in the presence of special hydrogenation catalysts. The invention is characterised by high enantioselectivity, providing easy access to a category of important pharmaceutical compositions, i.e. intermediates for the synthesis of tipranavir.

22 Claims, No Drawings

ENANTIOSELECTIVE HYDROGENATION OF INTERMEDIATES IN THE SYNTHESIS OF TIPRANAVIR

FIELD OF THE INVENTION

The present invention relates to a process for preparing intermediates in the synthesis of tipranavir, particularly enantioselective hydrogenation. Using this method it is easily possible to obtain intermediate products which can be used as starting compounds for the production of pharmaceutically effective compounds.

BACKGROUND TO THE INVENTION

Chirality plays a crucial part in numerous biological processes and has also acquired increasing importance for the pharmaceutical industry, as evidenced for example by the fact that of the drugs developed hitherto more than 80% have chiral properties. The various enantiomers may develop completely different effects in the body, so that only one of the enantiomeric forms is effective and is administered. For example, enzymes whose chiral components are the amino acids are able to distinguish between the individual enantiomeric forms in the body.

In particular, the enantiomers of 5,6-dihydro-4-hydroxy-2-pyrones are important structural elements in a number of pharmaceutically effective compounds, the category of the 5,6-dihydro-4-hydroxy-2-pyrone-sulphonamides being particularly important. Thus, [R-(R*,R*)]-N-[3-[1-[5,6-dihydro-4-hydroxy-2-oxo-6-(2-phenylethyl) -6-propyl-2H-pyran-3-yl]propyl]phenyl]-5-(trifluoromethyl)-2-pyridinesulphonamide, known as tipranavir (PNU-140690), is a protease inhibitor which is used to treat HIV and has the following structure:

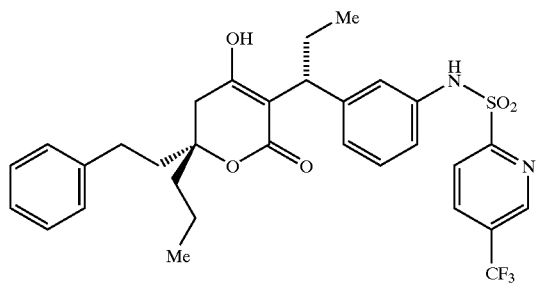

These and other structurally similar compounds are known from the prior art (cf. for example *J. Med. Chem.* 1998, 41, 3467–3476).

In order therefore to prepare active substances which are as optically isomerically pure as possible, particularly with respect to the above group of compounds, it is essential to develop selective methods of synthesis. This results in a large number of processes for preparing chiral compounds, for example separation processes such as crystallisation or chromatographic methods.

Non-selective synthesis requires an additional step of separating the optical isomers, e.g. in the form of a final racemate cleaving of the two enantiomers by either chemical or enzymatic methods. It is thus plain that selective syntheses which lead to only one optical isomer (either enantiomer or diastereomer) are advantageous. Thus, so-called asymmetric synthesis is increasingly used, i.e. preferably only one optical isomer is formed in a reaction. Enantio- or diastereoselective reactions are used not only in syntheses on a laboratory scale but also increasingly in industrial scale production.

One particularly elegant alternative method of preferentially synthesising an optical isomer is enantio- or diastereoselective catalysis with chiral catalysts. The catalysts are transition metal complexes with one or more chiral ligands. The number of possible chiral ligands is almost unimaginably great and therefore a number of combinations of metal and ligand(s) are opened up. However, this range of variation makes it difficult to arrive easily at the best combination for the product which is to be produced.

The development of new ligand systems is of enormous interest, particularly for use on an industrial scale, in terms of meeting the economic requirements such as cheap and efficient availability and high performance with regard to selectivity, yield and variability.

Asymmetric catalysis is important for a number of industrial processes and is used among other things in the production of amino acids and chiral amines and for ketone reduction. For example, the firm Degussa have developed the catalyst DeguPhos which is used for the reductive amination of alpha-keto acids, for preparing L- and D-amino acids. It is known that DuPhos ([1,5-cyclooctadiene) rhodium(I)-1,2-bis((2R,5R)-dimethyl-phospholano) benzene]tetrafluoroborate is used for the asymmetric hydrolysis of amino acids.

In addition, asymmetric hydrogenation is increasingly gaining importance as a chiral reaction. Some asymmetric hydrogenations are known on a laboratory scale for the production of small amounts but there are scarcely any large scale industrial processes in use. In order to adapt reactions of this kind to the industrial scale it is essential that the hydrogenation catalysts, particularly their ligands, have high selectivity and activity in addition to availability. Some proposals for enantioselective hydrogenation are known from the prior art: thus, the disclosure of WO 00/55150 describes a method of asymmetrically hydrogenating double bonds. Various intermediate products are prepared for the synthesis of tipranavir, while a rhodium catalyst with at least one chiral ligand containing a phosphorus atom is used. Preferably, DuPhos (1,2-bis((2R,5R)-dimethyl-phospholano)benzene) or BPE (1,2-bis((2R,5R)-dimethyl-phospholano)ethane) are used as chiral ligands.

U.S. Pat. Nos. 5,171,892, 5,532,395 or 5,559,267 describe the use of an enantioselective rhodium catalyst with DuPhos ligand, which is supposed to result in enantioselective hydrogenation in the range from 70 to 89%.

Moreover, the teaching of WO 99/12919 describes a process for preparing 4-hydroxy-2-oxo-pyran derivatives which includes, among other things, enantioselective hydrogenation with a catalyst containing DuPhos as ligand.

However, the transition metal complexes of chiral phosphane ligands mentioned above usually exhibit insufficient activity in catalytic processes of this kind, combined with only moderate stereoselectivity, with the result that it would frequently be preferable to use stoichiometric quantities of chiral hydride reagents. There is therefore still a need to develop a stereoselective hydrogenation catalyst which overcomes these disadvantages.

The problem of the invention is, therefore, as a continuation of the prior art, to provide a process which allows enantio- or diastereoselective hydrogenation in high yields, with a high enantio- or diastereoselectivity, with the lowest possible technical expenditure and a high space/time yield. This process should also be suitable for scaling up to an industrial scale, i.e. it should be cheap and therefore economical to carry out. Moreover, in the compounds which are provided according to the invention which are of central importance in the synthesis of the pharmaceutically active compounds mentioned above, the chiral information contained in the starting compounds should not be lost during hydrogenation and other groups present in the molecule should not be affected by the hydrogenation. Thus, a process according to the invention is to be provided by which only one specific double bond is selectively hydrogenated to form, if possible, only one optical isomer.

DETAILED DESCRIPTION OF THE INVENTION

Surprisingly, it has been found that the above-mentioned problem of the present invention is solved by a process for preparing the compounds of general formula I:

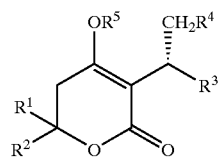

formula 1 wherein
$R^1$ and $R^2$ independently of one another denote hydrogen or a group which is selected from the group consisting of $C_1$–$C_6$-alkyl, $C_3$–$C_8$-cycloalkyl, $C_6$–$C_{10}$-aryl and $C_1$–$C_4$-alkylene-$C_6$–$C_{10}$-aryl, optionally with one, two or three substituents, selected from the group consisting of OH, $NH_2$, NH—CO—$CH_3$ or N(—CO—$CH_3)_2$, halogen, $C_1$–$C_4$-alkoxy and $CF_3$, while $R^1$ and $R^2$ do not simultaneously have the same meaning;

$R^3$ denotes an aryl substituted in the meta position, which optionally comprises at least one other substituent, the substituents being selected from the group consisting of F, Cl, Br, I, OH, O—$SO_2$—$CF_3$, $NO_2$, $NH_2$, NH—$SO_2$—(4-trifluoromethylpyridin-2-yl), N(—$CH_2$-aryl)$_2$, $NY_1Y_2$ with $Y_1$ and $Y_2$ selected from H, COO-alkyl, COO—$CH_2$-aryl, CO-alkyl and CO-aryl;

$R^4$ is selected from the group consisting of H and $C_1$–$C_8$-alkyl; and $R^5$ is selected from the group consisting of H, $Si(CH_3)_3$, Li, Na, K, Cs, $N(R')_4$, while all the R' groups may be identical or different and are selected from $C_1$–$C_8$-alkyl and $CH_2$-aryl;

by hydrogenating the compounds of general formula II:

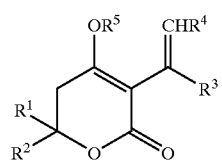

formula II wherein the groups $R^1$ to $R^5$ may have the meanings given above, in the presence of a catalyst which contains at least one ligand in the form of a chiral 1,2-bis(phospholano) maleic anhydride.

The starting compounds of general formula I are intermediates in the preparation of tipranavir and related products, which are used as starting compounds for the preparation of pharmaceutically active compounds. Mixtures of E/Z isomers (based on the double bond which is to be hydrogenated) may be used, from which surprisingly only one isomer is then selectively hydrogenated. Preferably a mixture of about 50% E and about 50% Z isomer is used.

According to a preferred variant of the invention, in general formulae I and II, $R^1$ and $R^2$ independently of one another may be selected from the group consisting of methyl, ethyl, propyl, butyl, phenyl, benzyl, cyclohexyl, phenylethyl and phenylpropyl, optionally with a substituent selected from the group consisting of hydroxy, fluorine, chlorine, bromine, methoxy, ethoxy and $CF_3$. Most preferably, $R^1$ denotes phenylethyl and $R^2$ denotes propyl or $R^1$ denotes propyl and $R^2$ denotes phenylethyl.

According to one embodiment which is particularly preferred according to the invention $R^1$ and $R^2$ are selected from phenylethyl and propyl, $R^3$ represents optionally substituted phenyl with an $NO_2$ group in the meta position, $R^4$ denotes methyl and $R^5$ denotes hydrogen. If there is another substituent at $R^3$ in addition to the meta substituent, it is preferable that it is selected from F, Cl, Br, I, OH or O—$SO_2$——$CF_3$.

In the present invention the term alkyl groups, including those which are part of other groups, denotes branched and unbranched alkyl groups with 1 to 4 carbon atoms, unless otherwise specified. Examples include the following hydrocarbon groups: methyl, ethyl, propyl, 1-methylethyl (isopropyl), n-butyl, 2-methylpropyl (iso-butyl), 1-methylpropyl (sec-butyl), 1,1-dimethylethyl (tert.-butyl). The terms propyl and butyl also include all the possible isomeric forms. In some cases common abbreviations are also used to denote the abovementioned alkyl groups, such as Me for methyl, Et for ethyl, Prop for propyl and But for butyl etc. The term alkylene groups in this case denotes branched and unbranched alkylene bridges with 1 to 4 carbon atoms. Examples include: methylene, ethylene, propylene and butylene. Unless otherwise stated, the terms propylene and butylene used above also include all the possible isomeric forms. Accordingly, the term propylene also includes the isomeric bridges n-propylene, methylethylene and dimethylmethylene and the term butylene includes the isomeric bridges n-butylene, 1-methylpropylene, 2-methylpropylene, 1,1-dimethylethylene and 1,2-dimethylethylene.

The cycloalkyl group is intended according to the invention to denote a saturated cyclic hydrocarbon group with 3 to 8 carbon atoms. Cyclic hydrocarbons with 3 to 6 carbon atoms are preferred. Examples are cyclopropyl, cyclobutyl, cyclopentyl, cyclohexyl, cycloheptyl and cyclooctyl.

Alkyloxy, which may optionally also be referred to as alkoxy, denotes within the scope of the invention a straight-chain or branched alkyl group with 1 to 4 carbon atoms bound via an oxygen atom. The methoxy group is particularly preferred.

The term aryl denotes an aromatic ring system with 6 to 10 carbon atoms. Preferred aryl groups are naphthyl and phenyl, the phenyl group being particularly preferred. The abbreviations Naph for naphthyl and Ph for phenyl are optionally used. By aryl-alkylene or alkylene-aryl are meant, for the purposes of the invention, aryl groups linked via an alkylene bridge, while the abovementioned definitions apply to alkylene groups and aryl groups. Preferred alkylene-aryl groups according to the invention, unless otherwise specified, are benzyl, 2-phenylethyl and 3-phenylpropyl.

The term halogen generally denotes fluorine, chlorine, bromine or iodine, of which fluorine, chlorine and bromine are preferred, unless stated otherwise.

The starting compounds of general formula I described above are enantioselectively hydrogenated in the presence of a catalyst. It is known that the hydrogenation of a molecule is influenced by other chiral centres present in the molecule. However, this is not the case with the present compounds of formula I. According to the invention, therefore, the catalyst in this enantioselective hydrogenation is of crucial importance. It allows the compounds of the above formula I to be synthesised directly from the compounds of formula II, without any further intermediate steps or laborious separation of the isomeric forms.

Enantioselective hydrogenation in this context should also include diastereoselective hydrogenation, as there may be another chiral centre in the compounds of general formula I. The skilled man knows what is meant by this in the present case, however.

The catalyst of the invention contains, as explained previously, a transition metal ion, such as rhodium-(I), ruthenium-(I), iridium-(I) or another suitable transition metal, rhodium-(I) being preferred. This transition metal is coordinated with at least one ligand in the form of a chiral 1,2-bis(phospholano)maleic anhydride.

By this 1,2-bis(phospholano)maleic anhydride according to the present invention is meant, most preferably, the system of general formula III formula III

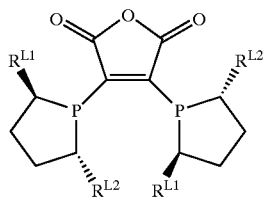

wherein $R^{L1}$ and $R^{L2}$ which may be identical or different denote branched or unbranched $C_1$–$C_8$-alkyl, preferably $C_1$–$C_4$-alkyl, particularly preferably methyl, ethyl or isopropyl.

Particularly preferred according to the invention is a system of formula III wherein $R^{L1}$ and $R^{L2}$ have the same meanings, and particularly preferably both represent methyl. The last-named compound of formula III mentioned as being particularly preferred, wherein $R^{L1}$ and $R^{L2}$ both represent methyl, is also known by the name MalPhos in the prior art.

The above-mentioned chiral 1,2-bis(phospholano)maleic anhydride is an optionally substituted bidentate bisphospholane system, i.e. two five-membered saturated rings each having one phosphorus atom in the ring—the so-called phospholane systems—are bound to the double bond of a maleic anhydride via the two phosphorus atoms. Such ligands are known by the trade name MalPhos. The transition metal forms a complex with the ligand, which can be used as a hydrogenation catalyst.

According to another preferred embodiment the catalyst has the following structure:

[ligand¹-transition metal-ligand²] anion, wherein the ligand¹ denotes the chiral 1,2-bis(phospholano) maleic anhydride of formula III shown above. Preferably the ligand² is an unsaturated cyclic hydrocarbon with 3 to 12 carbon atoms, while cyclopentadiene, benzene, cycloheptatriene or cyclooctadiene systems are preferably used. Most preferably, cyclopentadiene or 1,5-cyclooctadiene (COD) is used as the ligand².

The ligand² may be substituted with one or more organic groups. In a preferred embodiment according to the invention the ligand² is unsubstituted. If on the other hand the ligand² is substituted, straight-chain or branched $C_1$–$C_8$-alkyl groups, particularly $C_1$–$C_4$-alkyl groups may be used as substituents.

In the catalyst used according to the invention there is preferably an anion as counter-ion to the transition metal-cation complex, such as for example $BF_4^-$, $CF_3$—CO—O$^-$, Cl$^-$, Br$^-$ or I$^-$, of which the $BF_4^-$ adduct is preferred.

The following formula represents the hydrogenation catalyst which is particularly preferred in the process according to the invention, the MalPhos-rhodium-1,5-cyclooctadiene-tetrafluoroborane adduct:

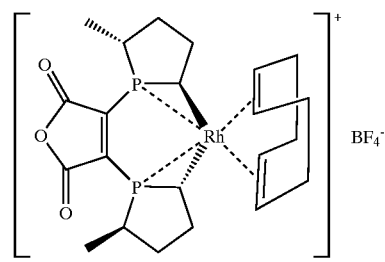

It is known that the enantioselectivity of the hydrogenation is influenced by the catalyst used, but with such complex systems predictions as to correlations between structure and activity are only possible in a few isolated cases. In the development of chiral ligands which may be used in such complexes, the steric data play a part, such as for example a certain conformational rigidity of the complex. Apart from the steric parameters of the phospholanes, which together with the ligand backbone co-determine the overall structure and fix the geometry of the metal binding site, the electronic properties of the donor atoms (σ/π donor/acceptor capacity) are a second variable which crucially determines the properties of catalytically active transition metal complexes. Moreover the overall electronic character of the ligand appears to be important.

Fine tuning of the conformational, steric and electronic properties of the ligands is admittedly possible at considerable expense but because of the numerous different influences no systematic conclusions can readily be drawn as to the effectiveness and suitability of a particular catalyst.

Apart from the chemical and physical properties of the ligands the costs of the transition metal and ligands and the activity and stability of the catalyst also play a part, as well as the possibility of recovering them and re-using them after suitable working up. Moreover, catalysts are not readily commercially obtainable and first have to be prepared by laborious processes. These considerations weigh heavily, particularly in large-scale industrial processes.

In view of the above findings a very large number of tests were carried out to find a catalytic system which meets the desired requirements to a high degree. According to the invention, a hydrogenation catalyst was successfully used in the process provided, which not only has excellent activity and stability and is cheap to produce, but also leads to the desired products in a highly enantioselective manner. Thus, using the process according to the invention, enantioselective hydrogenation is achieved in the region of more than about 90 %, preferably more than about 95%, particularly preferably more than about 98%.

The process according to the invention will now be described in detail:

The starting compounds according to the above general formula I are intermediates in the synthesis of tipranavir, which can be further processed after enantioselective hydrogenation has taken place. The starting compound of formula I may be used either in the form of an isomer or as a mixture of E and Z isomers.

With some substituents, the hydrogenation has to be carried out in the presence of a base. This is the case, for example, if $R^5$ denotes a hydrogen atom or a $Si(CH_3)_3$ group. This is part of the general knowledge of the skilled man, who knows when it is necessary to use a corresponding base.

Preferably, the base is selected from the group consisting of a hydroxide, $C_1$–$C_5$-alkoxide, bicarbonate, carbonate, di- and tribasic phosphate, borate, fluoride, amine optionally substituted with $C_1$–$C_4$-alkyl or aryl, silane optionally substituted with $C_1$–$C_3$-alkyl. Particularly preferably, the base is an alkali metal or alkaline earth metal methoxide, ethoxide or carbonate, more preferably a carbonate. Particularly preferred alkali metal or alkaline earth metal alkoxides or carbonates are those of sodium, potassium, calcium or magnesium, while those of sodium and potassium, particularly sodium, are of exceptional importance according to the invention.

It has proved particularly advantageous if the base is used in an amount of about 1 mol % to about 20 mol %, preferably about 5 mol % to about 15 mol %.

It is advisable to carry out the hydrogenation under an inert gas atmosphere. Suitable media are nitrogen gas or a noble gas such as argon, nitrogen being preferred for reasons of cost.

The hydrogenation according to the invention is advantageously carried out in a solvent. Suitable solvents according to the invention are those normally used for reactions of hydrogenation. Examples include: methanol, ethanol, acetone, methylene chloride, ethyl acetate, toluene, xylene and acetonitrile. Methanol and ethanol are particularly preferred as the solvent.

It has proved particularly advantageous to add the catalyst to the reaction mixture last. However, this is not essential in every case. The amount of catalyst used is preferably about 0.001 mol % to about 5 mol %, preferably about 0.01 mol % to about 0.5 mol %, particularly about 0.05 mol % to about 0.15 mol %. This results in a ratio (in mol) of substrate/catalyst of about 200/1 to 5000/1, preferably about 500/1 to about 3000/1, particularly about 1000/1 to about 2000/1.

According to a preferred embodiment the catalyst is first dispersed or dissolved in a solvent and then added to the reaction mixture containing the compound to be hydrogenated, solvent and optionally a base. Preferably the same solvent is then used for the catalyst and the reaction mixture. The catalyst may, however, also be added without a solvent.

Hydrogenation starts after or during the addition of the catalyst. The hydrogenation in the process according to the invention is preferably carried out in a temperature range from about 20° C. to about 100° C., preferably about 40° C. to about 80° C., particularly preferably between about 50° C. and about 70° C., most particularly preferably at about 60° C. If there are sensitive reaction groups in the molecule it is particularly advisable for the temperature not to exceed about 100° C., or in individual cases 80° C. For example a nitro group present in the molecule is reduced to the amino group at temperatures above about 80° C., which may be undesirable. Temperatures below about 20° C. slow the reaction down to the extent that it is no longer economically viable.

Within the scope of the hydrogenation according to the invention the pressure level set is not particularly restricted. This serves essentially to increase the speed of the reaction. However, it is advisable to set the hydrogen pressure for the hydrogenation in the range from about 2 bar to about 200 bar, preferably about 10 bar to about 50 bar, particularly preferably between about 15 bar and about 40 bar.

The hydrogenation according to the invention is preferably carried out for a reaction period of about 1 h to about 100 h, more preferably about 5 h to about 40 h, particularly preferably about 1 h to about 30 h. According to the invention, therefore, it is possible to achieve an enantioselectivity of above about 90%, preferably above about 95%, and even above about 98% with a relatively short reaction period of about 24 h. This demonstrates the clear superiority over the systems known hitherto in the art, which do not exhibit this degree of selectivity.

The hydrogenated product obtained may be subjected to additional purification, for example one or more washing steps and/or recrystallisation from the solvent used, and may be separated off and worked up in the usual way.

The skilled man given the task will have no difficulty in selecting and setting the most suitable reaction conditions, such as temperature, pressure, solvent, reaction time and the like for the particular hydrogenation and optimising these conditions accordingly, by means of a few guiding experiments.

The advantages associated with the invention are numerous: The process according to the invention provides a simple means of access to isomers which were previously relatively difficult to obtain, and also allows this to be done on a large industrial scale with excellent productivity. The process according to the invention makes it possible to prepare the desired product not only in high yields but also with very high enantioselectivity. No additional purification steps are needed, the products may be further processed directly just as they occur.

The hydrogenation catalyst according to the invention exhibits a high performance, particularly in the form of its excellent activity and stability, and is highly enantioselective, so that the desired products are easily obtained. Using the process according to the invention enantioselectivity is achieved in the region of more than about 90 %, preferably more than about 95%, most preferably more than about 98%. Starting from the E/Z isomer mixture laborious separation into the two isomers can thus be avoided; rather, only the desired isomer is obtained in hydrogenated form, and the process works not only on the laboratory scale but also in large industrial plants.

The economic requirements for large-scale industrial use, such as high performance in terms of selectivity, yield and variability are thus met by the catalyst according to the invention in a high degree. In addition, the catalysts used in the hydrogenation processes of the invention are cheap to produce. Thus, the starting products for the preparation of MalPhos are significantly cheaper, compared with the starting materials for DuPhos, with the result that even the manufacture of the catalyst is much cheaper.

The efficiency of the catalyst system used according to the invention is clearly superior to that of the prior art. Thus, for example, reactions catalysed with rhodium-Malphos systems progress faster and with higher enantioselectivity, compared with the corresponding DuPhos systems.

According to the invention, therefore, a class of important pharmaceutical compositions, the non-peptidic HIV-protease inhibitors, such as tipranavir, are easily accessible, so that the technical teaching of the invention constitutes a valuable addition to the pharmaceutical sector.

The invention is hereinafter described specifically by means of an Example, which should not restrict the teaching according to the invention. Additional embodiments will become apparent to the skilled man from the disclosure according to the invention.

EXAMPLE 1

Enantioselective hydrogenation according to the invention was carried out starting from the following compound 1:

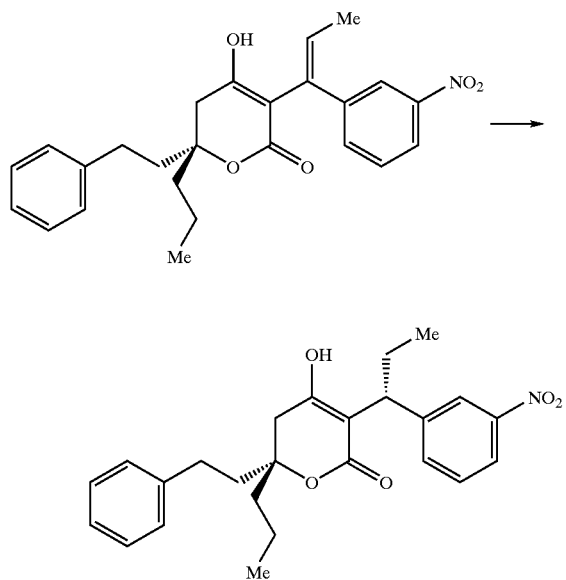

compound 1 diastereoselectively hydrogenated compound 1
MW=421.50 MW=423.51
empirical formula $C_{25}H_{27}NO_5$ empirical formula: $C_{25}H_{29}NO_5$ The hydrogenation was carried out as follows:

67 g of compound 1, 270 ml of methanol and 1.7 g of sodium carbonate were placed in a 500 ml autoclave. After it had been rendered totally inert a solution of 96.8 mg of Malphos-[Rh(COD)]-$BF_4$ in 10 ml of degassed methanol was added under nitrogen. Then the mixture was stirred for approx. 24 h at approx. 60° C. under approx. 10 bar hydrogen pressure.

The hydrogenating solution was washed with 14 ml methanol into a glass reactor, heated to approx. 50° C. and adjusted to a pH of approx. 1.4 with hydrochloric acid (32%). For 2 h, 61 ml of water were added dropwise at approx. 50° C. Then the mixture was cooled to 20° C. for 3 h, stirred for 1.5 h at this temperature and finally the crystalline product was suction filtered. It was washed again with 133 ml of methanol/water (2:1) and dried at approx. 45° C. in vacuo, producing about 50.5 g (approx. 80%) of the hydrogenated compound 1.

Chemical and optical purity:>98% ($^1$H-NMR).

What is claimed is:
1. A process for preparing a compound of the formula I:

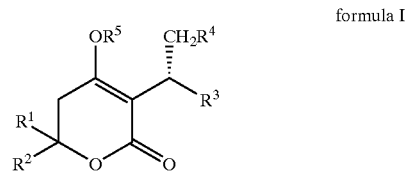

wherein
$R^1$ and $R^2$ independently of one another denote hydrogen or a group which is selected from among the group consisting of $C_1$–$C_6$-alkyl, $C_3$–$C_8$-cycloalkyl, $C_6$–$C_{10}$-aryl and $C_1$–$C_4$-alkylene-$C_6$–$C_{10}$-aryl, optionally with one, two or three substituents, selected from the group consisting of OH, $NH_2$, NH—CO—$CH_3$ or N(—CO—$CH_3$)$_2$, halogen, $C_1$–$C_4$-alkoxy and $CF_3$, while $R^1$ and $R^2$ do not simultaneously have the same meaning;
$R^3$ denotes an aryl substituted in the meta position, which optionally comprises at least one other substituent, the substituents being selected from the group consisting of F, Cl, Br, I, OH, O—$SO_2$—$CF_3$, $NO_2$, $NH_2$, NH—$SO_2$-(4-trifluoromethylpyridin-2-yl), N(—$CH_2$-aryl)$_2$, $NY_1Y_2$ with $Y_1$ and $Y_2$ selected from H, COO-alkyl, COO—$CH_2$-aryl, CO-alkyl and CO-aryl;
$R^4$ is selected from the group consisting of H and $C_1$–$C_8$-alkyl; and
$R^5$ is selected from the group consisting of H, Si($CH_3$)$_3$, Li, Na, K, Cs, N(R')$_4$, while all the R' groups may be identical or different and are selected from $C_1$–$C_8$-alkyl and $CH_2$-aryl;
which process comprises hydrogenating a compound of the formula II

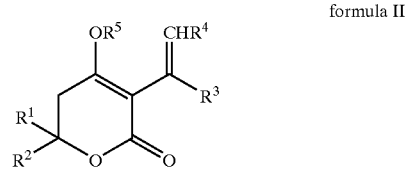

wherein the groups $R^1$ to $R^5$ are as previously defined in this claim, in the presence of a catalyst which contains at least one ligand in the form of a chiral 1,2-bis(phospholano) maleic anhydride.

2. The process according to claim 1, wherein $R^1$ and $R^2$ independently of one another are selected from the group consisting of methyl, ethyl, propyl, butyl, phenyl, benzyl, cyclohexyl, phenylethyl and phenylpropyl, optionally with a substituent selected from the group consisting of hydroxy, fluorine, chlorine, bromine, methoxy, ethoxy and $CF_3$.

3. The process according to 1, wherein $R^1$ denotes phenylethyl and $R^2$ denotes propyl or $R^1$ denotes propyl and $R^2$ denotes phenylethyl.

4. The process according to claim 1, wherein $R^1$ and $R^2$ are selected from phenylethyl and propyl, $R^3$ denotes optionally substituted phenyl with an $NO_2$ group in the meta position, $R^4$ denotes methyl and $R^5$ denotes hydrogen.

5. The process according to claim 1, wherein the starting compound of the formula I is used in the form of an E/Z mixture.

6. The process according to claim 5, wherein roughly 50:50 mixture of E and Z isomer is used.

7. The process according to claim 1 wherein the catalyst has the following structure:

[ligand$^1$-transition metal-ligand$^2$] anion, wherein the ligand$^1$ denotes a chiral 1,2-bis(phospholano) maleic anhydride of formula III

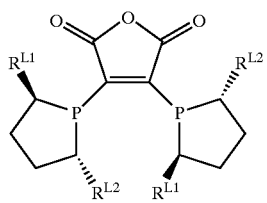

formula III wherein $R^{L1}$ and $R^{L2}$ which may be identical or different represent branched or unbranched $C_1$–$C_8$-alkyl.

8. The process according to claim 7, wherein the ligand$^2$ denotes an unsaturated cyclic hydrocarbon with 3 to 12 carbon atoms.

9. The process according to claim 7, wherein the ligand$^2$ denotes a cyclopentadiene, benzene, cycloheptatriene or cyclooctadiene system.

10. The process according to claim 9, wherein the ligand$^2$ denotes cyclopentadiene or 1,5-cyclooctadiene.

11. The process according to claim 7, wherein the ligand$^1$ of formula III, $R^{L1}$ and $R^{L2}$ represent branched or unbranched $C_1$–$C_4$-alkyl.

12. The process according to claim 11, wherein $R^{L1}$ and $R^{L2}$ both represent methyl.

13. The process according to claim 7, characterised in that the transition metal in the catalyst is rhodium-(I), ruthenium-(I) or iridium-(I).

14. The process according to claim 7, wherein the anion in the catalyst is $BF_4^-$, $CF_3$—CO—$O^-$, $Cl^-$, $Br^-$ or $I^-$.

15. The process according to claim 1 wherein it is carried out in the presence of the following catalyst:

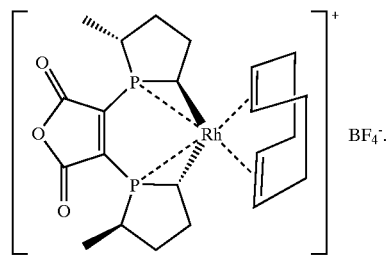

16. The process according to claim 1 wherein the hydrogenation is carried out in the presence of a base.

17. The process according to claim 16, wherein the base is selected from the group consisting of a hydroxide, $C_1$–$C_5$-alkoxide, bicarbonate, carbonate, di- and tribasic phosphate, borate, fluoride, optionally with $C_1$–$C_4$-alkyl or aryl-substituted amine optionally substituted with $C_1$–$C_4$-alkyl or aryl or silane optionally substituted with $C_1$–$C_3$-alkyl.

18. The process according to claim 16 wherein the base is selected from alkali metal or alkaline earth metal methoxide, ethoxide or carbonate.

19. The process according to claim 16 wherein the base is used in an amount of about 1 mol % to about 20 mol %.

20. The process according to claim 1 wherein the ratio (in mol) of substrate/catalyst is about 200/1 to 5000/1.

21. The process according to claim 1 wherein the temperature during hydrogenation is about 20° C. to about 100° C.

22. The process according to claim 1 wherein the hydrogen pressure during hydrogenation is about 2 bar to about 100 bar.

* * * * *